United States Patent [19]
Clawson

[11] Patent Number: 6,053,864
[45] Date of Patent: *Apr. 25, 2000

[54] METHOD AND SYSTEM FOR GIVING REMOTE EMERGENCY MEDICAL COUNSEL TO ARREST PATIENTS

[76] Inventor: Jeffrey J. Clawson, 4649 Farm Meadow La., Salt Lake City, Utah

[*] Notice: This patent issued on a continued prosecution application filed under 37 CFR 1.53(d), and is subject to the twenty year patent term provisions of 35 U.S.C. 154(a)(2).

[21] Appl. No.: 08/829,468
[22] Filed: Mar. 28, 1997

Related U.S. Application Data

[60] Provisional application No. 60/014,741, Mar. 29, 1996.

[51] Int. Cl.[7] ................................................. A61B 5/00
[52] U.S. Cl. ................................. 600/300; 128/920
[58] Field of Search .................. 128/920, 923, 128/924, 903, 904, 905; 600/408, 300; 364/922, 922.2, 922.3, 922.4

[56] References Cited

U.S. PATENT DOCUMENTS

| | | | |
|---|---|---|---|
| 4,130,881 | 12/1978 | Haessler et al. | 364/900 |
| 4,237,344 | 12/1980 | Moore | 179/2 A |
| 4,290,114 | 9/1981 | Sinay | 364/900 |
| 4,360,345 | 11/1982 | Hon | 434/262 |
| 4,489,387 | 12/1984 | Lamb et al. | 364/514 |
| 4,731,725 | 3/1988 | Suto et al. | 364/415 |
| 4,839,822 | 6/1989 | Dormond et al. | 364/513 |
| 4,858,121 | 8/1989 | Barber et al. | 364/406 |
| 4,945,476 | 7/1990 | Bodick et al. | 364/413.02 |
| 5,063,522 | 11/1991 | Winters | 395/51 |
| 5,065,315 | 11/1991 | Garcia | 364/413.01 |
| 5,072,383 | 12/1991 | Brimm et al. | 364/413.02 |
| 5,086,391 | 2/1992 | Chambers | 364/413.02 |
| 5,228,449 | 7/1993 | Christ et al. | 128/691 |
| 5,253,164 | 10/1993 | Holloway et al. | 364/406 |
| 5,255,187 | 10/1993 | Sorensen | 364/413.02 |
| 5,404,292 | 4/1995 | Hendrickson | 364/413.02 |
| 5,462,051 | 10/1995 | Oka et al. | 128/630 |
| 5,471,382 | 11/1995 | Tallman et al. | 364/406 |
| 5,521,812 | 5/1996 | Feder et al. | 364/400 |
| 5,544,649 | 8/1996 | David et al. | 128/630 |
| 5,594,638 | 1/1997 | Lliff | 395/203 |
| 5,596,994 | 1/1997 | Bro | 128/732 |
| 5,660,176 | 8/1997 | Lliff | 128/630 |

*Primary Examiner*—Francis J. Jaworski
*Attorney, Agent, or Firm*—Lloyd W. Sadler

[57] ABSTRACT

A method and system for providing emergency medical counseling to arrest patients remotely is described. A consistent, standard and systematic process is provided which in combination with adequate training, supervision and quality assurance serves to provide a method for gathering emergency medical information regarding providing emergency medical dispatch services to arrest patients, categorizing such information into various determinant levels for appropriate response, and for giving qualified emergency medical information to callers thereby permitting "zero time" response by those at the scene. By using this invention properly a dispatcher is guided through the interrogation of callers concerned with arrest patients, gathering critical information and giving the appropriate guidance to the caller. This invention specifically guides the dispatcher through the steps of the procedure for giving remote emergency medical counsel to arrest patients, thereby providing the "zero time" response by utilizing those at the scene of the arrest emergency.

3 Claims, 9 Drawing Sheets

(ARREST ADULT)

& nbsp;
METHOD AND SYSTEM FOR GIVING REMOTE EMERGENCY MEDICAL COUNSEL TO ARREST PATIENTS This application claims priority from Provisional Application number 60/014,741, filed Mar. 29, 1996.

SOFTWARE APPENDIX

This specification includes a software appendix which includes an enabling description of one preferred embodiment of the design and implementation of the process of the invention in the computer software alternative embodiment of the invention. This appendix is produced herein to provide programmers of ordinary skill in the arts of emergency medical procedures and computer programming all information necessary to enable their coding, use and practice of the software embodiment of the invention. In other embodiments of the invention, the inventive concept may be implemented in other computer code, in computer hardware, in other circuitry, in a combination of these, in a reference card or flowchart format not involving computer technology at all, or otherwise. An alternative preferred embodiment of the invention is a reference card format. The software appendix is hereby incorporated by reference in its entirety and is considered to be a part of the disclosure of this specification.

BACKGROUND OF THE INVENTION

1. Field of the Invention

This invention relates to methods and systems for processing and responding to emergency medical inquiries. Specifically, this invention relates to the process of providing emergency medical counsel, instruction or advice to callers who are inquiring concerning medical arrest cases. Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing consistent and proven advice and instruction for persons on the scene with patients in medical arrest. This invention, in its best mode of operation, operates as part of a system for the management, processing and response of an emergency medical dispatch system. This emergency medical dispatch system accomplishes the above objectives by: First, gathering necessary medical complaint information from emergency medical inquiry callers and providing emergency verbal instructions to individuals at the scene. Second, prioritizing the complaint to determine the criticality of the emergency. Third, assisting dispatched responders to be prepared for each emergency situation. Fourth, advising those on the way to provide care at the scene of specific problems or potential hazards. When used correctly this invention decreases the effective response time, while increasing the professionalism and control of emergency medical dispatchers, increases the accuracy and appropriateness of patient interrogation and well as the quality of gathered information, reduces the number of multiple unit responses thereby reducing the risk of emergency medical vehicular collisions, improves patient care, reduces burn-out and stress of dispatchers by improving their quality of training, decreases the risk of responder injury or mistake by providing responders with improved knowledge of the situation, provides an means for continuously improving the quality of emergency patient care, and provides a "zero-time" emergency medical response through guidance given remotely, typically over a telephone, to individual at the scene.

While being included within a greater invention that addresses all of the above issues, this invention specifically addresses the method or process of giving emergency medical counsel to arrest patients and/or those individuals at the scene with the patient. Arrest is a critical medical condition where rapid correct response is essential to the successful treatment of the patient. This invention is especially important since the travel time for an emergency medical team to the patient is often to long for the team to be able to give the most effective treatment. This invention provides a means for communicating, in an orderly manner, to individuals at the scene the information necessary to help them revive the patient. Accurate, efficient and systematic responses to calls for help with medical arrest situations can and does make the difference in the successful resolution of such incidents.

2. Description of Related Art

It is desirable to provide a systematic and standardized method for responding to emergency medical requests, especially where the patient is suffering an arrest and individuals at the scene can if properly instructed help the patient. Although in the related art some attempt has been made to address the problem of medical care assessment, the related art does not address the specific problems of emergency dispatcher response to medical problems related to arrest Rather related art approaches describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein.

SUMMARY OF THE INVENTION

It is desirable to provide a system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation. Furthermore, it is desirable to have an emergency medical dispatch system that includes provisions for instructing, counseling, advising those on the scene in procedures and techniques that can aid in reviving an arrest patient. It is desirable to have such provisions which incorporate proven techniques for guiding an on-scene individual through the process and which includes a scripted procedure which steps the dispatcher through the process without depending solely on the individual skills and knowledge base of the dispatcher.

Accordingly, it is the primary object of this invention to provide a medical dispatch system that is designed to guide the medical dispatcher through the interrogation, obtaining vital patient information regarding calls concerning patients in arrest.

Another object of this invention is to provide a cross-referenced scripted set of instructions to be given by the dispatcher to the caller in an arrest medical emergency situation.

A further object of this invention is to improve the quality, efficiency and usefulness of the information received to and communicated by emergency medical dispatchers thereby improving the quality of emergency medical services provided to patient before, during and after the arrival of emergency medical technicians.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provides. Each preferred embodiment incorporates the same essential method of this invention, though each has its own particular advantages.

DETAILED DESCRIPTION OF THE INVENTION

This invention provides a method, system and an apparatus for receiving, processing and communicating emergency medical information, specifically related to communicating instructions to individuals at the scene for the emergency treatment of arrest victim patients. When the invention is properly employed the initial interrogation of the caller or patient will have previously provided the emergency medical dispatcher critical patient information which has indicated that the patient is most likely suffering from an arrest. This information has been applied in protocols which have led the dispatcher through a scripted interrogation, gathering additional related information, and categorizing the problem by assigning a determinant value establishing the criticality of the problem. This invention then functions by providing appropriate scripted established emergency medical instruction to the individuals on the scene.

This invention includes three protocol processes, each focusing on the specific needs of arrest victims of particular ages, infants less than one year old; children from one to seven years old; and adults eight or more years old. Although three processes are involved, each incorporates a nearly identical procedure, which is this invention. Each process or protocol is merely a particular alternative preferred embodiment of the invention, modified to fit the particular requirements of arrest victims of specific ages.

Figure 1:
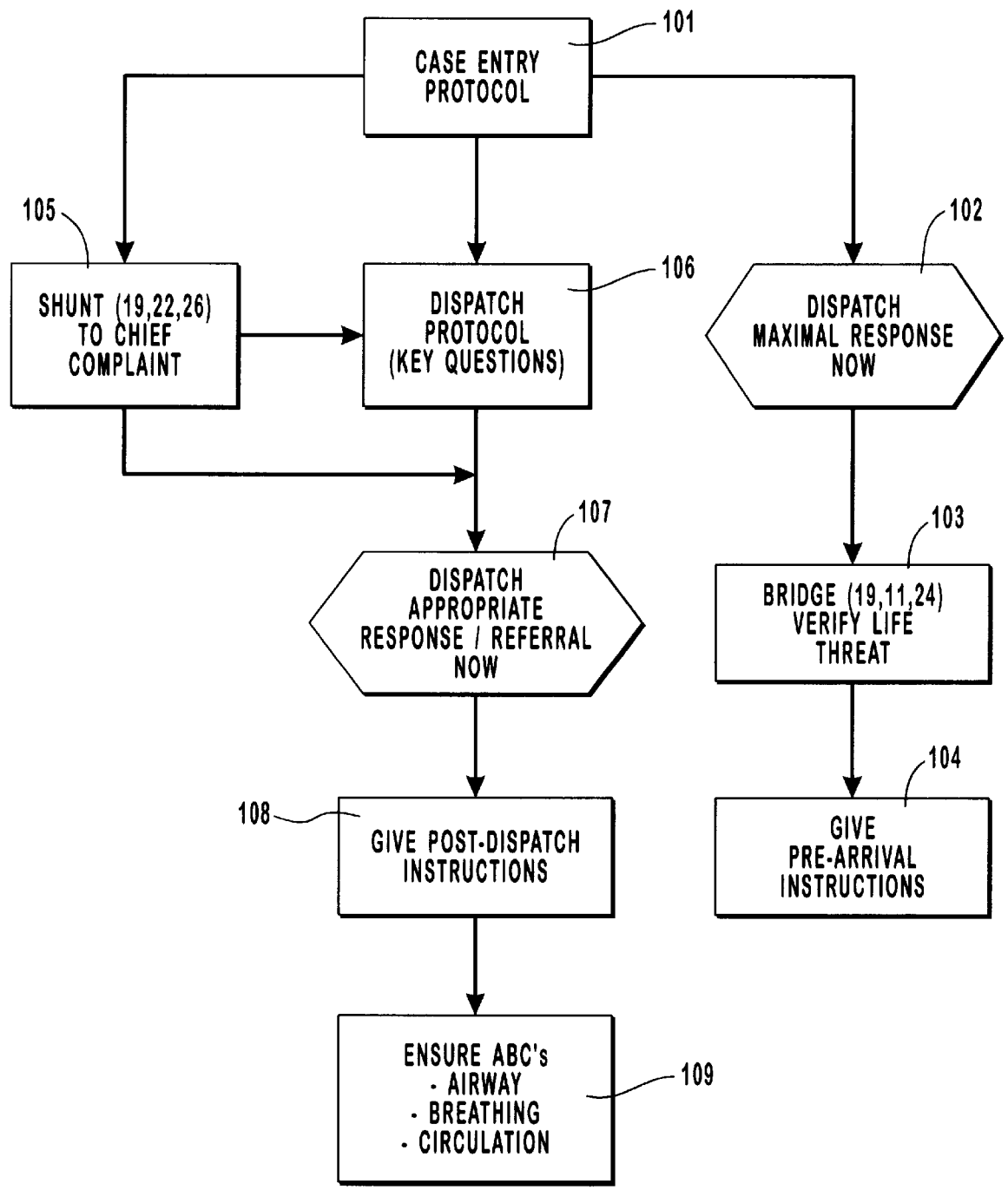
FIG. 1 depicts the principle elements of the complete system in which the preferred embodiment of the invention operates and the relationship of the elements of system to each other, and serves to put this invention in the context of the complete system.

FIG. 1 shows the complete system in which the invention operates in its best mode. The process of managing emergency medical dispatchers, the information they require and the information they give is detailed in FIG. 1. The case entry protocol 101 provides the initial steps through which the all emergency callers or patients are taken to provide symptom information and to access medical information. The purpose of the case entry protocol 101 is to receive sufficient information to permit the dispatcher to identify the caller's chief complaint This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. A maximum response dispatch 102 may include such resources as emergency medical technicians, ambulances, paramedics, and other appropriate medical care givers. The life threat is then verified 103 and pre-arrival instructions are given 104. These pre-arrival instructions 104 include six treatment sequence scripts covering Arrest, Choking, and Childbirth. The pre-arrival instruction procedure for arrest is the heart of this invention. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha—A, Bravo—B, Charlie—C, and Delta—D) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
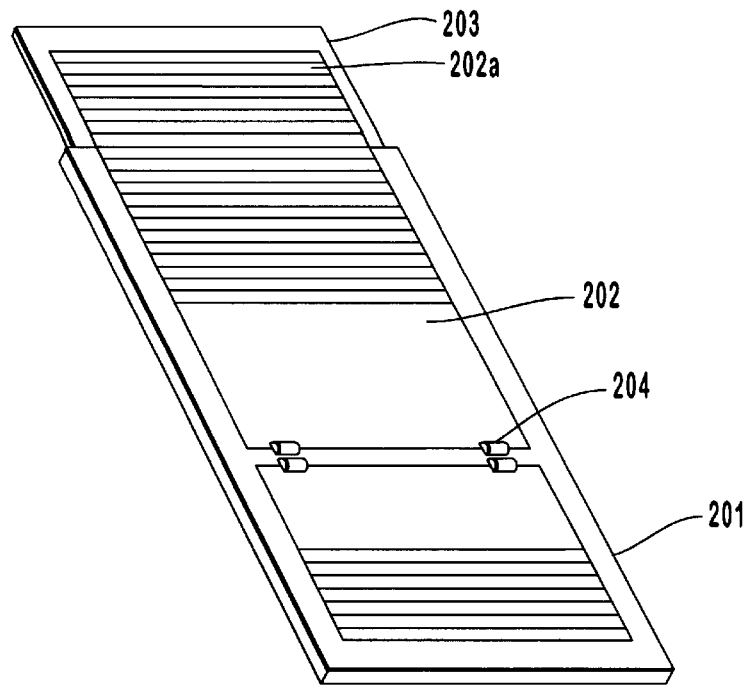
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202a. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
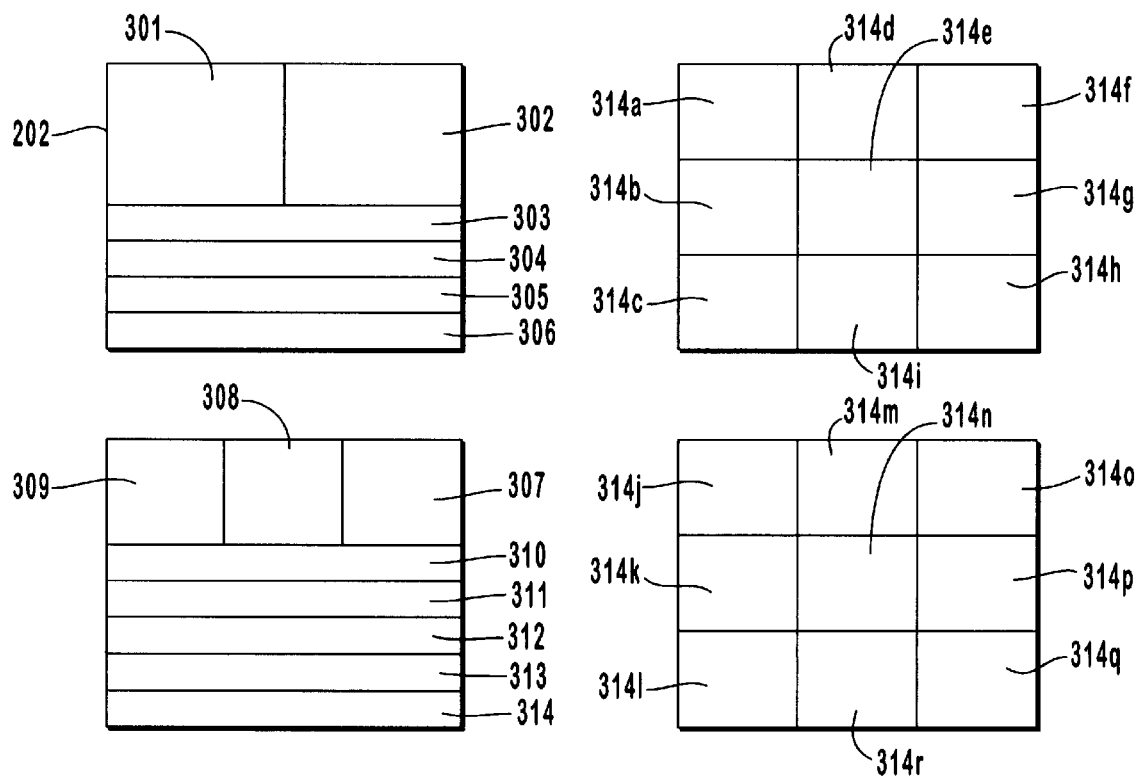
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A—Alpha 303, B—Bravo 304, C—Charlie 305 and D—Delta 306 are provided to aid the dispatcher in making the determinant designation. Each determinant level may have one or more sublevels. Generally, the most critical call is given a determinant level of D—Delta and the least critical call is given a determinant level of A—Alpha The more critical the determinant level assigned to a call, the more medical resources and urgency may be applied to provide help. For example, an A—Alpha call will typically be responded to by emergency medical technicians and an ambulance proceeding to the patient under the safest method reasonably possible, while a D—Delta call will typically be responded to by the closest emergency medical technicians, an ambulance, paramedics, all who will proceed under the most urgent method possible.. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene and prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314 *a–r*. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
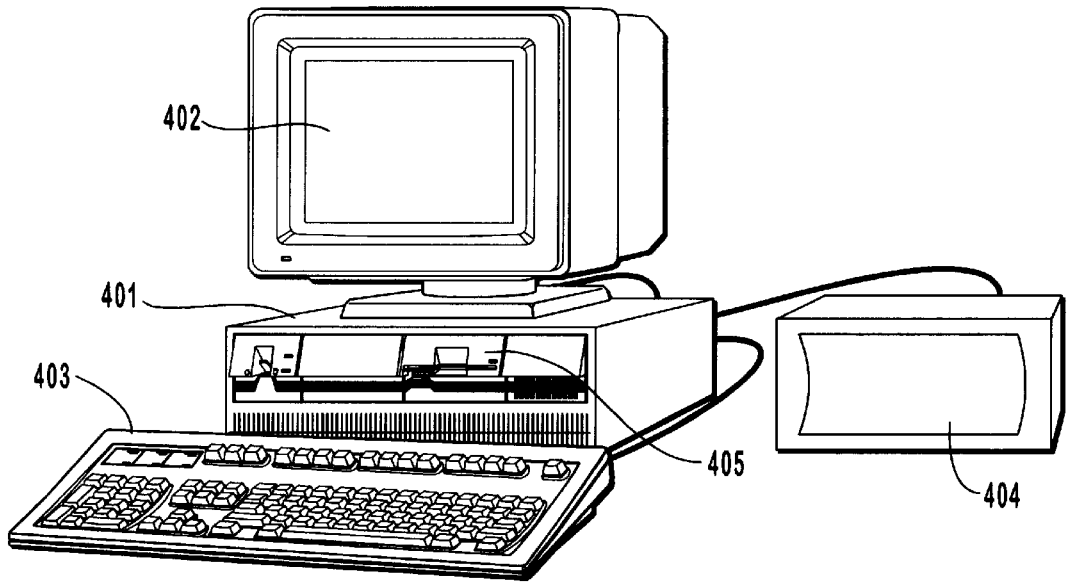
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
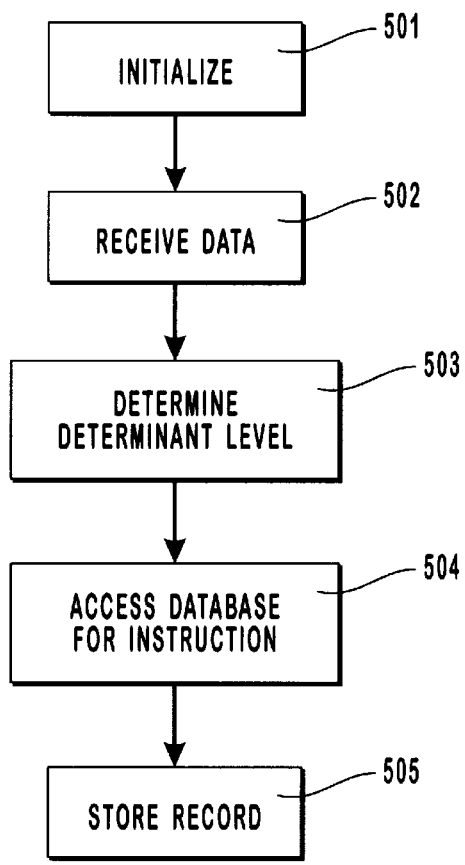
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
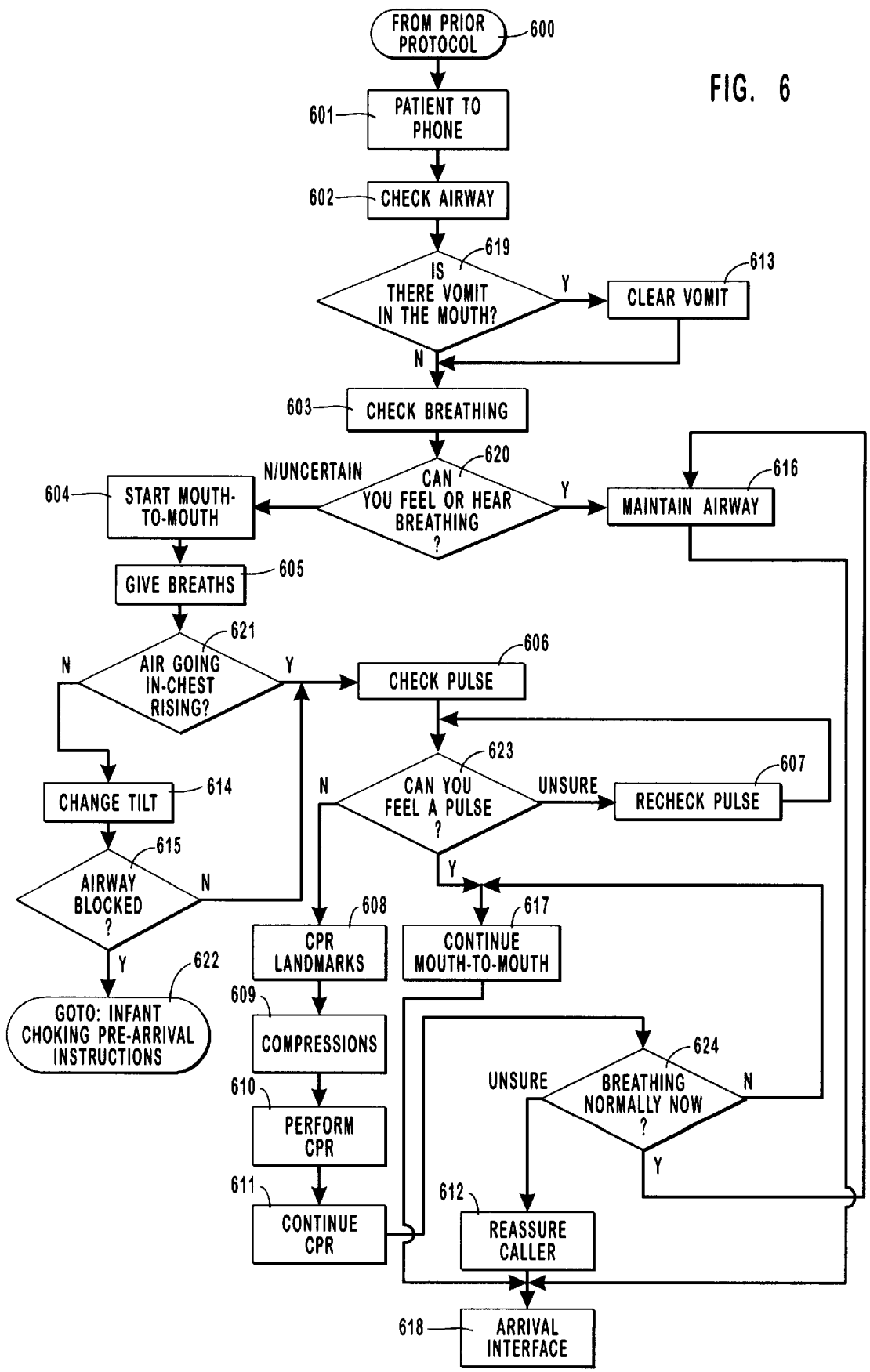
FIG. 6 depicts the detailed steps of the arrest pre-arrival instructions protocol process for infants less than one year old, constituting the preferred embodiment of the invention for these patients.

FIG. 6 depicts the detailed steps of the arrest pre-arrival instruction protocol for infants, in a form reflecting the preferred embodiment of the invention. Although the following steps of the protocol process of the invention need not necessarily be accomplished in this specific order, alternative ordering of the steps of the invention are possible, this order of the steps of the process has been determined by the inventor to be the best mode of the invention. First, this protocol of pre-arrival instructions for arrested infants is reached, in the best mode of the invention, after the dispatcher has interrogated the caller, determined the type of medical emergency, assigned a determinant value describing the level of emergency and, in general, after the dispatcher has dispatched an emergency medical response team to the site of the arrest emergency. The following procedure of this invention is performed as a systematic means of providing interim emergency medical instruction to individuals at the scene. Therefore, this invention is generally reached from a prior emergency medical protocol 600. After each step the caller is instructed to "Do it now and then come right back to the phone." The caller is instructed to bring the patient as close to the phone as possible 601. During this step the caller is also informed that he or she is going to be instructed on how to do CPR and not to hang up. The caller is asked where the baby is now. Next the caller is instructed to perform the check airway step 602, in the following manner. First, put the baby on his or her back on the floor. Remove any pillows. Place one hand under the neck and shoulders and slightly tilt the head back. Look into the mouth. Do it now and come back to the phone to report. The caller is then asked if there is vomit in the baby's mouth 619. If there is vomit in the baby's mouth the caller is instructed to clear the vomit 613 by turning the baby's head to the side and cleaning out his or her mouth. If the vomit has been cleared then the caller is instructed to check the baby's breathing 603, by putting the caller's ear next to the baby's mouth. Listen and feel for any breathing or if the baby's chest rises. The caller is asked, "can you feel or hear any breathing?" 620. If the caller cannot hear of be certain of the baby's breathing the caller is instructed on giving mouth-to-mouth 604. The mouth-to-mouth instruction includes: "place your hand under the neck and shoulders and slightly tilt the baby's head back. Completely cover the baby's mouth and nose with your mouth." The caller is instructed to give breaths 605, by blowing two soft puffs of air into the lungs, just like your are blowing up a small balloon. The caller is instructed to watch for the baby's chest to rise with each breath. The caller is asked whether the caller can feel the air going in or see the baby's chest rising 621. If the caller cannot tell if air is going in, the caller is instructed to change the tilt 614 of the baby's head back a little more. Then the caller is instructed to cover the baby's mouth and nose with the callers mouth, blowing two soft puffs of air into the lungs, just like you are blowing up a small balloon. After which the caller is asked if the baby's airway is blocked 622. If it is, the dispatcher goes to the infant choking pre-arrival instruction protocol, specifically concerned with performing the Heimlich maneuver on the baby. If the baby's airway is not blocked or if the air is observed going into the baby, then the caller is instructed to check the baby's pulse 606. This instruction is given in the following manner. "Place your index and middle fingers over the baby's left nipple. Feel carefully for a pulse. Don't press to hard. Feel for five seconds." The caller is asked if he or she can feel a pulse 623. If the caller is not certain whether there is a pulse, the caller is told to recheck for a pulse 607, by using the caller's index finger and middle fingers to feel carefully for about five seconds on the inside of the baby's upper arm. If the caller cannot feel a pulse, the caller is instructed to prepare for CPR 608, by placing two fingers in the center of the baby's chest, right between the nipples. Then the caller is told to compress the chest 609 by pushing down 1 inch with only your fingers touching the chest; pumping the baby's chest rapidly five times. Next, the caller is instructed to perform CPR 610 by tilting the baby's head back again with the caller's hand under the baby's neck and shoulders, putting the caller's mouth over the baby's nose and mouth, giving one soft puff then pumping the baby's chest five more times, making sure the caller's fingers are on the bone in the center of the chest, right between the nipples. The caller is next instructed to continue CPR 611 by continuing repeating this cycle of one puff and five pumps, until help can take over. If the baby starts breathing, the dispatcher asks to be told immediately. A question is asked as to whether the baby is breathing normally now 624. If the caller is uncertain, the caller is reassured 612 and told not to give up, to keep repeating the cycle of one puff and five pumps. If the caller says that the baby is not breathing normally, the dispatcher instructs the caller to continue mouth-to-mouth 617. If the baby starts breathing normally, the caller is instructed to maintain the baby's airway 616, by keeping the baby's head tilted back and by watching the baby very closely to be sure he or she is breathing all right. If anything changes or if the baby starts making "funny noises" the caller is instructed to tell the dispatcher immediately. Lastly, the caller is instructed to prepare for the arrival of the paramedics through the arrival interface step 618, by telling the caller not to stop CPR until the paramedics take over and to hand the phone to one of the paramedics as soon as they arrive. Also, the caller is instructed to make sure that the door is unlocked and if possible that someone should open it for the paramedics.

Figure 7:
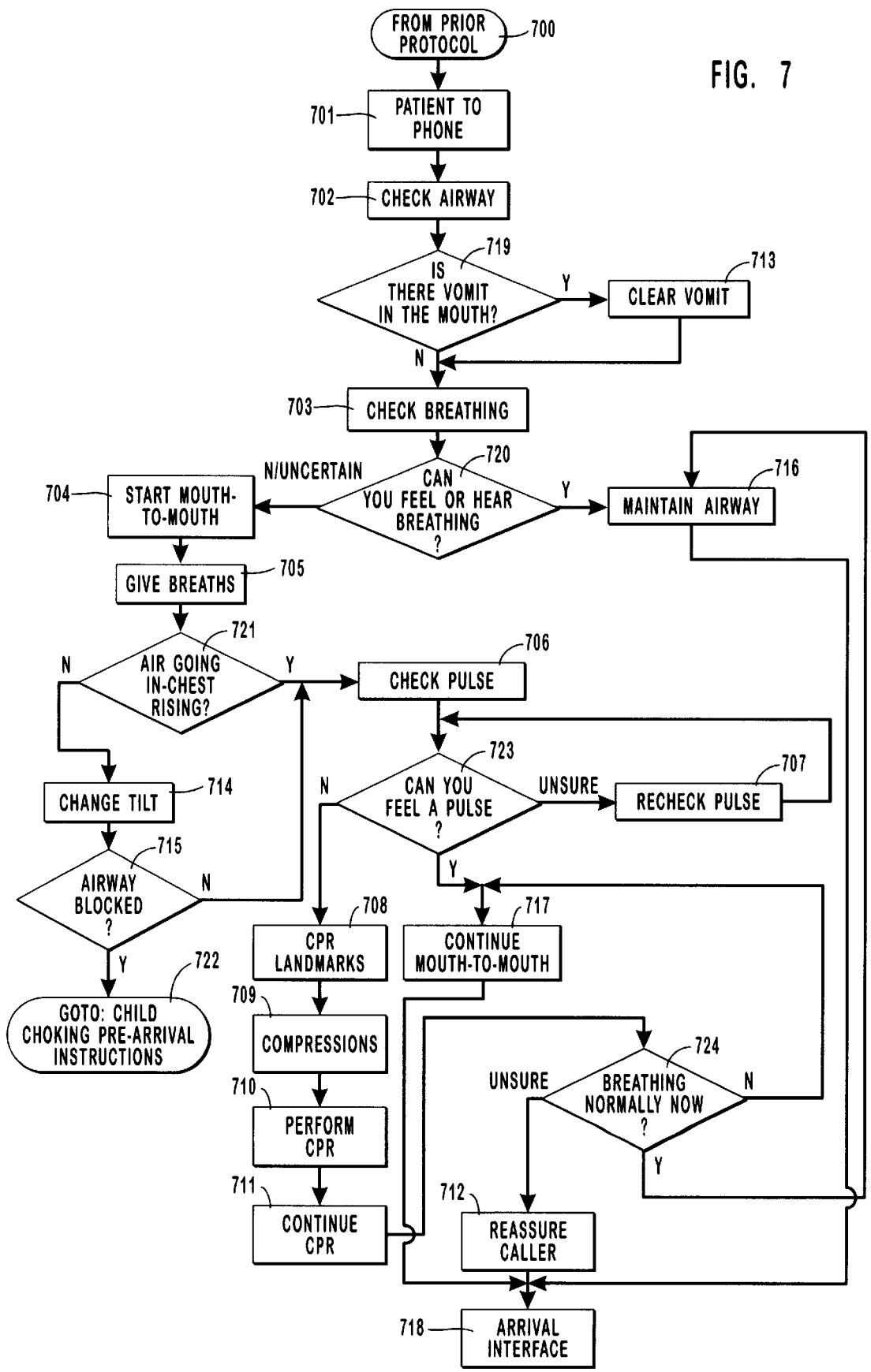
FIG. 7 depicts the detailed steps of the arrest pre-arrival instructions protocol process for children, ages one to seven years, constituting the preferred embodiment of the invention for these patients.

FIG. 7 depicts the detailed steps of the arrest pre-arrival instruction protocol for children, in a form reflecting the preferred embodiment of the invention. Although the following steps of the protocol process of the invention need not necessarily be accomplished in this specific order, alternative ordering of the steps of the invention are possible, this order of the steps of the process has been determined by the inventor to be the best mode of the invention. First, this protocol of pre-arrival instructions for arrested children is reached, in the best mode of the invention, after the dispatcher has interrogated the caller, determined the type of medical emergency, assigned a determinant value describing the level of emergency and, in general, after the dispatcher has dispatched an emergency medical response team to the site of the arrest emergency. The following procedure of this invention is performed as a systematic means of providing interim emergency medical instruction to individuals at the scene. Therefore, this invention is generally reached from a prior emergency medical protocol 700. After each step the caller is instructed to "Do it now and then come right back to the phone." The caller is instructed to bring the patient as close to the phone as possible 701. During this step the caller is also informed that he or she is going to be instructed on how to do CPR and not to hang up. The caller is asked where the child is now. Next the caller is instructed to perform the check airway step 702, in the following manner. First, put the child on his or her back on the floor. Remove any pillows. Place one hand under the neck and shoulders and tilt the head back. Look into the mouth. Do it now and come back to the phone to report. The caller is then asked if there is vomit in the child's mouth 719. If there is vomit in the child's mouth the caller is instructed to clear the vomit 713 by turning the child's head to the side and cleaning out his or her mouth. If the vomit has been cleared then the caller is instructed to check the child's breathing 703, by putting the caller's ear next to the child's mouth. Listen and feel for any breathing or if the child's chest rises. The caller is asked, "can you feel or hear any breathing?" 720. If the caller cannot hear or be certain of the child's breathing, the caller is instructed on giving mouth-to-mouth 704. The mouth-to-mouth instruction includes: "place your hand under the neck and shoulders and slightly tilt the child's head back. Pinch the child's nose closed. Completely cover the child's mouth with your mouth." The caller is instructed to give breaths 705, by blowing two soft breaths of air into the lungs, just like your are blowing up a balloon. The caller is instructed to watch for the child's chest to rise with each breath. The caller is asked whether the caller can feel the air going in or see the child's chest rising 721. If the caller cannot tell if air is going in, the caller is instructed to change the tilt 714 of the child's head back a little more. Then the caller is instructed to cover the child's mouth with the callers mouth, blowing two soft breaths of air into the lungs, just like you are blowing up a balloon. After which the caller is asked if the child's airway is blocked 722. If it is, the dispatcher goes to the child choking pre-arrival instruction protocol, specifically concerned with performing the Heimlich maneuver on a child age one to seven. If the child's airway is not blocked or if the air is observed going into the child, then the caller is instructed to check the child's pulse 706. This instruction is given in the following manner. "Slide your index and middle fingers into the groove next to the Adam's apple. Feel carefully for a pulse. Don't press to hard. Feel for five seconds." The caller is asked if he or she can feel a pulse 723. If the caller is unsure whether there is a pulse, the caller is told to recheck for a pulse 707, by trying the other side of the neck. Feeling carefully for five seconds again. If the caller cannot feel a pulse, the caller is instructed to prepare for CPR 708, by putting the heel of one hand on the breastbone in the center of the child's chest, right between the nipples. Then the caller is told to compress the chest 709 by pushing down 1½ inches with only the heel of one hand touching the child's chest. Doing it five times, just like the caller is pumping the child's chest twice a second. Next, the caller is instructed to perform CPR 710 by pinching the child's nose closed and tilting his or her head back again with the caller's hand under the childs's neck and shoulders, putting the caller's mouth over the child's mouth, giving one soft breath then pumping the child's chest five more times, making sure the caller's hand is on the bone in the center of the chest, right between the nipples. The caller is next instructed to continue CPR 711 by continuing repeating this cycle of one breath and five pumps, until help can take over. The dispatcher asks to be told immediately if the child starts breathing. A question is asked as to whether the child is breathing normally now 724. If the caller is unsure, the caller is reassured 712 and told not to give up, to keep repeating the cycle of one breath and five pumps. If the caller says that the child is not breathing normally, the dispatcher instructs the caller to continue mouth-to-mouth 717. If the child starts breathing normally, the caller is instructed to maintain the child's airway 716, by keeping the child's head tilted back and by watching the child very closely to be sure he or she is breathing all right. If anything changes or if the baby starts making "funny noises" the caller is instructed to tell the dispatcher immediately. Lastly, the caller is instructed to prepare for the arrival of the paramedics through the arrival interface step 718, by telling the caller not to stop CPR until the paramedics take over and to hand the phone to one of the paramedics as soon as they arrive. Also, the caller is instructed to make sure that the door is unlocked and if possible that someone should open it for the paramedics.

Figure 8:
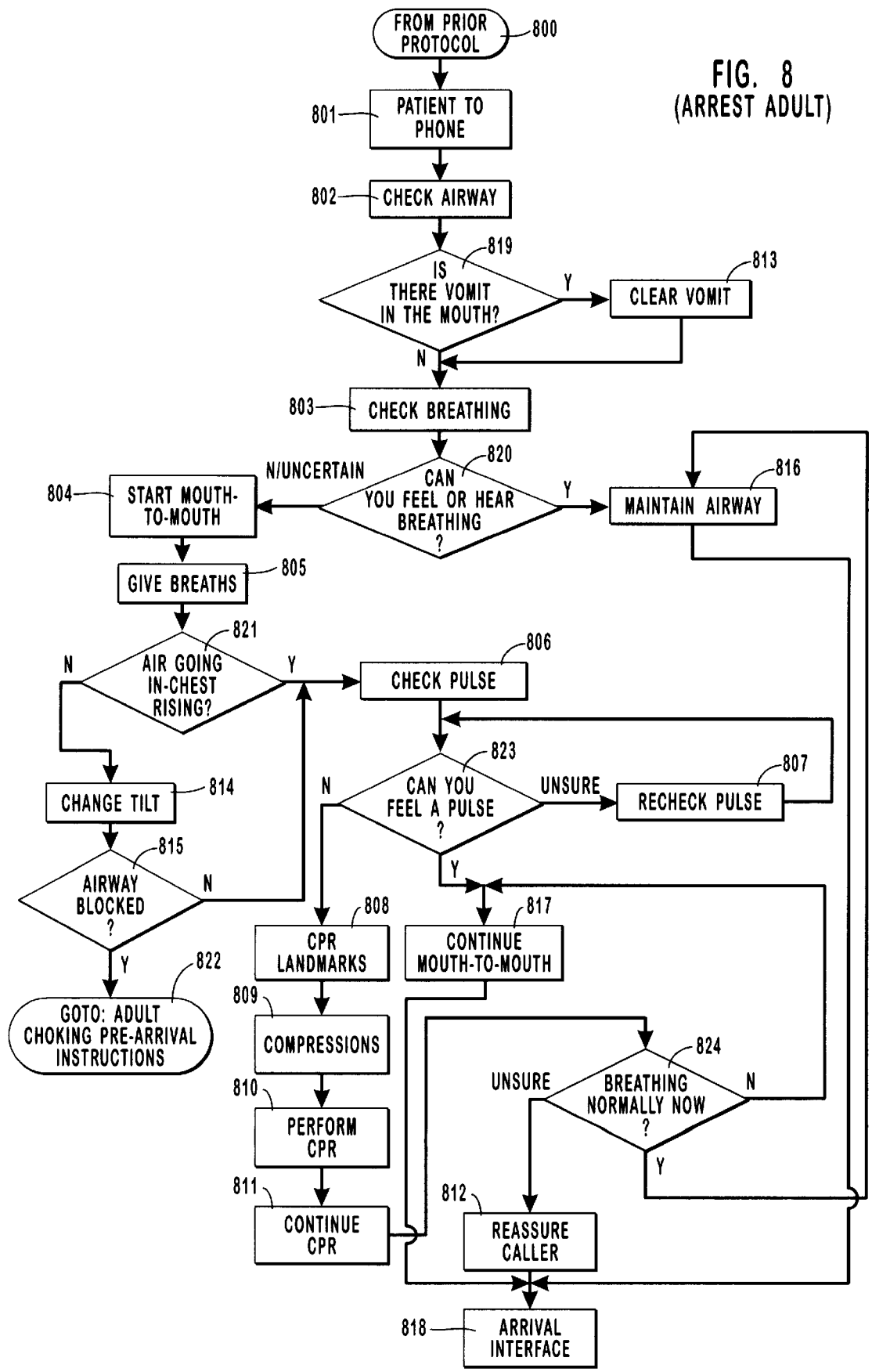
FIG. 8 depicts the detailed steps of the arrest pre-arrival instructions protocol process for adults, ages eight and older, constituting the preferred embodiment of the invention for these patients.

FIG. 8 depicts the detailed steps of the arrest pre-arrival instruction protocol for adults, in a form reflecting the preferred embodiment of the invention. Although the following steps of the protocol process of the invention need not necessarily be accomplished in this specific order, alternative ordering of the steps of the invention are possible, this order of the steps of the process has been determined by the inventor to be the best mode of the invention. First, this protocol of pre-arrival instructions for arrested adults is reached, in the best mode of the invention, after the dispatcher has interrogated the caller, determined the type of medical emergency, assigned a determinant value describing the level of emergency and, in general, after the dispatcher has dispatched an emergency medical response team to the site of the arrest emergency. The following procedure of this invention is performed as a systematic means of providing interim emergency medical instruction to individuals at the scene. Therefore, this invention is generally reached from a prior emergency medical protocol 800. After each step the caller is instructed to "Do it now and then come right back to the phone." The caller is instructed to bring the patient as close to the phone as possible 801. During this step the caller is also informed that he or she is going to be instructed on how to do CPR and not to hang up. The caller is asked where the patient is now. Next the caller is instructed to perform the check airway step 802, in the following manner. First, put the patient on his or her back on the floor. Remove any pillows. Place one hand under the neck and the other on the forehead and tilt the head back. Look into the mouth. Do it now and come back to the phone to report. The caller is then asked if there is vomit in the patient's mouth 819. If there is vomit in the patient's mouth the caller is instructed to clear the vomit 813 by turning the patient's head to the side and cleaning out his or her mouth. If the vomit has bee cleared then the caller is instructed to check the patient's breathing 803, by putting the caller's ear next to the patient's mouth. Listen and feel for any breathing or if the patient's chest rises. The caller is asked, "can you feel or hear any breathing?" 820. If the caller cannot hear of be certain of the patient's breathing the caller is instructed on giving mouth-to-mouth 804. The mouth-to-mouth instruction includes: "place one hand under the neck and the other on the patient's forehead and tilt the patient's head back. Pinch the patient's nose closed. Completely cover the patient's mouth with your mouth." The caller is instructed to give breaths 805, by blowing two deep breaths of air into the lungs, just like your are blowing up a big balloon. The caller is instructed to watch for the patient's chest to rise with each breath. The caller is asked whether the caller can feel the air going in or see the patient's chest rising 821. If the cannot tell if air is going in, the caller is instructed to change the tilt 814 of the patient's head back a little more. Then the caller is instructed to cover the patient's mouth with the callers mouth, blowing two deep breaths of air into the patient's lungs, just like you are blowing up a large balloon. After which the caller is asked if the patient's airway is blocked 822. If it is, the dispatcher goes to the adult choking pre-arrival instruction protocol, specifically concerned with performing the Heimlich maneuver on the patient. If the patient's airway is not blocked or if the air is observed going into the patient, then the caller is instructed to check the patient's pulse 806. This instruction is given in the following manner. "Slide your index and middle fingers into the grove next to the Adam's apple. Feel carefully for a pulse. Don't press to hard. Feel for five seconds." The caller is asked if he or she can feel a pulse 823. If the caller is not certain whether there is a pulse, the caller is told to recheck for a pulse 807, by trying the other side of the neck. Feeling carefully for five seconds again. If the caller cannot feel a pulse, the caller is instructed to prepare for CPR 808, by placing the heel of the caller's hand on the breastbone in the center of the patient's chest, right between the nipples. Then the caller is told to compress the chest 809 by pushing down firmly 2 inches with only heel of the caller's lower hand touching the chest; do it fifteen times, just like pumping. Next, the caller is instructed to perform CPR 810 by pinching the patient's nose closed and tilting his or her head back again. Giving two more big breaths, then pumping the chest fifteen more times, making certain the heel of the caller's hand is on the bone in the center of the patient's chest, right below the nipples. The caller is next instructed to continue CPR 811 by continuing repeating this cycle of two breaths and fifteen pumps, until help can take over. The dispatcher asks to be told immediately, if the patient starts breathing. A question is asked as to whether the patient is breathing normally now 824. If the caller is unsure, the caller is reassured 812 and told not to give up, to keep repeating the cycle of two breaths and fifteen pumps. If the caller says that the patient is not breathing normally, the dispatcher instructs the caller to continue mouth-to-mouth 817. If the patient starts breathing normally, the caller is instructed to maintain the patient's airway 816, by keeping the patient's head tilted back and by watching him or her very closely to be sure he or she is breathing all right. If anything changes or if the patient starts gurgling or making "funny noises" the caller is instructed to tell the dispatcher immediately. Lastly, the caller is instructed to prepare for the arrival of the paramedics through the arrival interface step 818, by telling the caller not to stop CPR until the paramedics take over and to hand the phone to one of the paramedics as soon as they arrive. Also, the caller is instructed to make sure that the door is unlocked and if possible that someone should open it for the paramedics.

Figure 9:
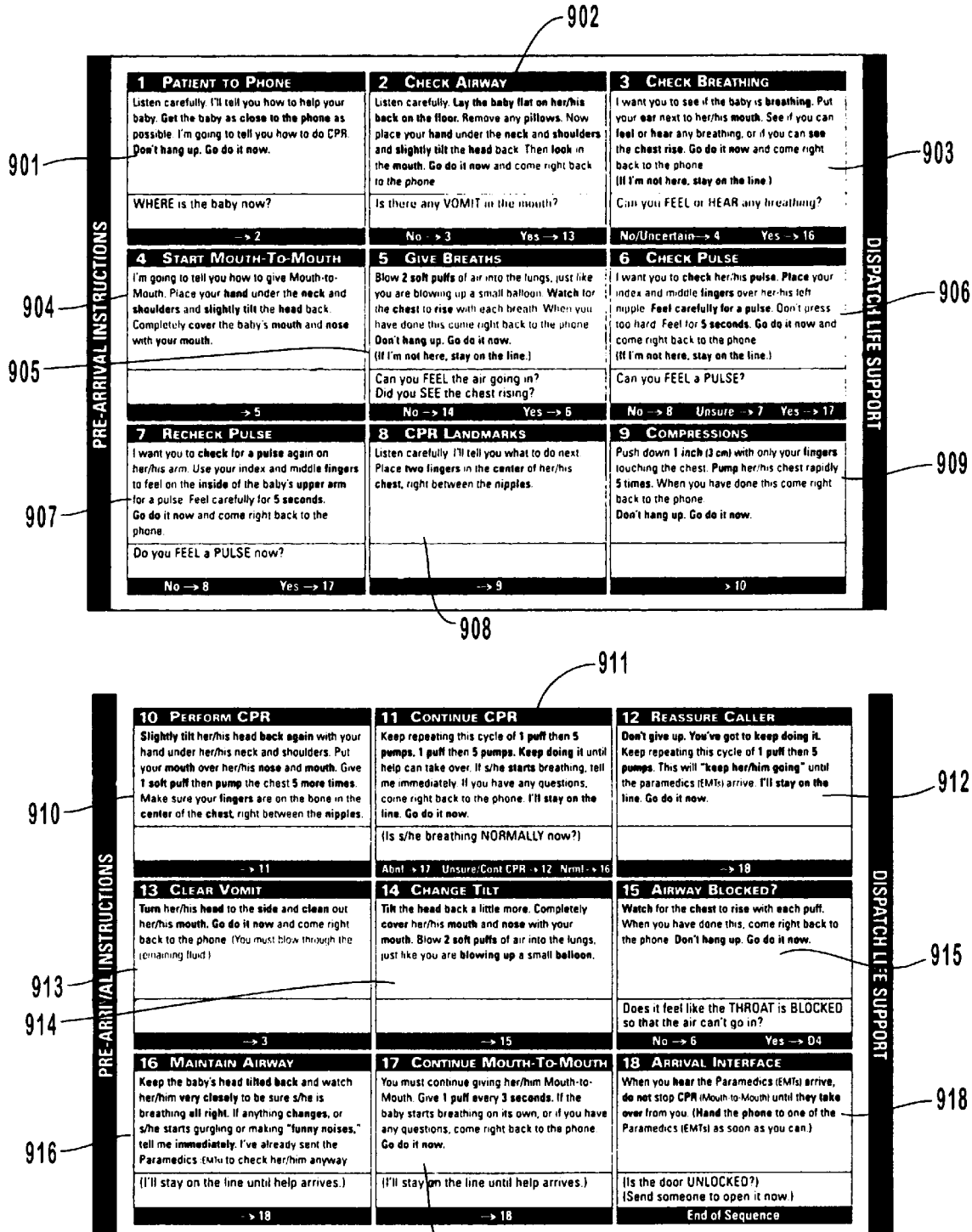
FIG. 9 depicts the preferred embodiment of the flip cards used as one embodiment of this invention, which shows the steps of the arrest-infant pre-arrival instructions protocol of the flip card deck embodiment of the invention..

FIG. 9 depicts the preferred embodiment of the flip cards showing the steps of the arrest—infant pre-arrival instruction protocol invention. The patient to phone step is shown 901. The check airway step is shown 902. The check breathing step is shown 903. The start mouth-to-mouth step is shown 904. The give breaths step is shown 905. The check pulse step is shown 906. The recheck pulse step is shown 907. The CPR landmarks step os shown 908. The compressions step is shown 909. The perform CPR step is shown 910. The continue CPR step is shown 911. The reassure caller step is shown 912. The clear vomit step is shown 913. The change tilt step is shown 914. The airway blocked step is shown 915. The maintain airway step is shown 916. The continue mouth-to-mouth step is shown 917. The arrival interface step is shown 918.

Figure 10:
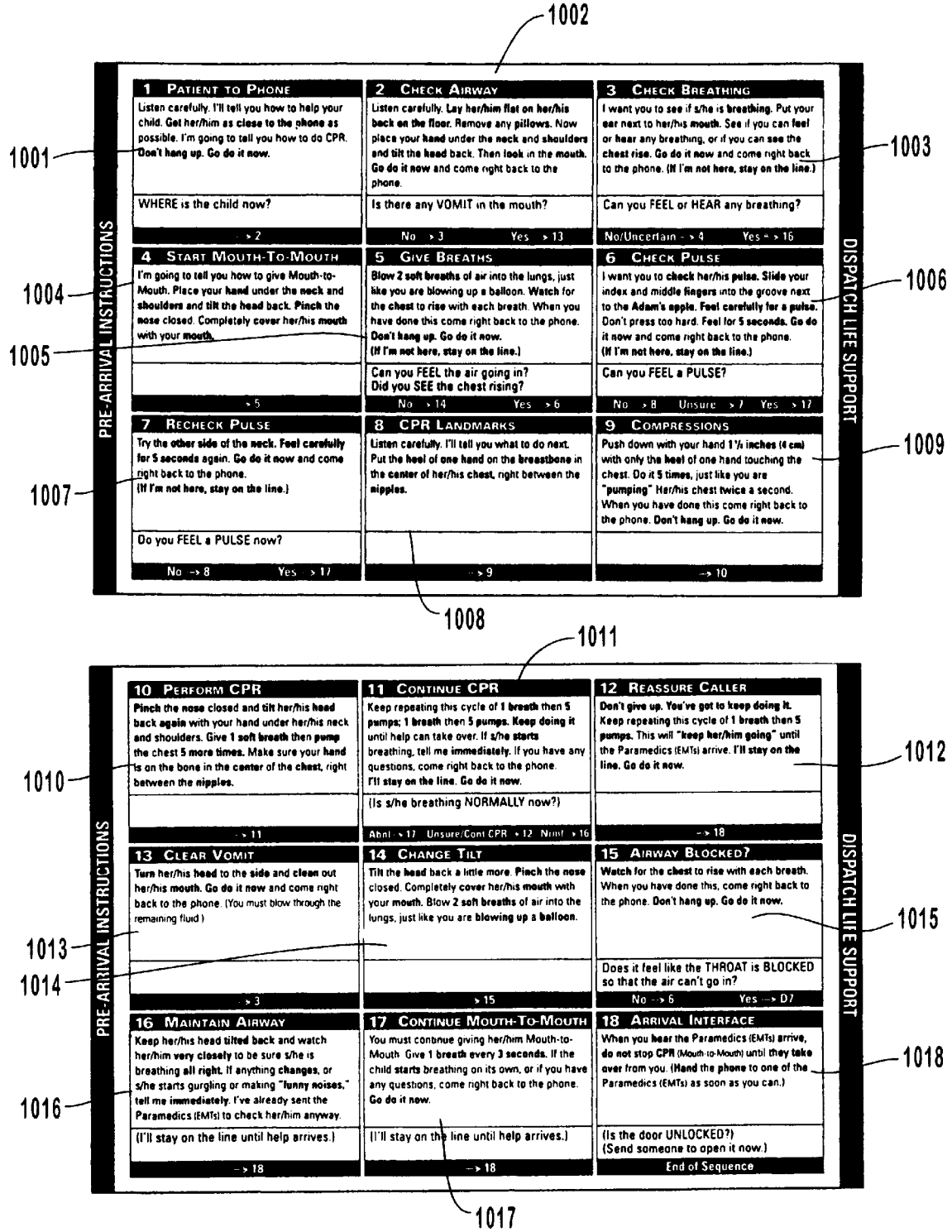
FIG. 10 depicts the preferred embodiment of the flip cards used as one embodiment of this invention, which shows the steps of the arrest-child pre-arrival instructions protocol of the flip card deck embodiment of the invention.

FIG. 10 depicts the preferred embodiment of the flip cards showing the steps of the arrest—child pre-arrival instruction protocol invention. The patient to phone step is shown 1001. The check airway step is shown 1002. The check breathing step is shown 1003. The start mouth-to-mouth step is shown 1004. The give breaths step is shown 1005. The check pulse step is shown 1006. The recheck pulse step is shown 1007. The CPR landmarks step os shown 1008. The compressions step is shown 1009. The perform CPR step is shown 1010. The continue CPR step is shown 1011. The reassure caller step is shown 1012. The clear vomit step is shown 1013. The change tilt step is shown 1014. The airway blocked step is shown 1015. The maintain airway step is shown 1016. The continue mouth-to-mouth step is shown 1017. The arrival interface step is shown 1018.

Figure 11:
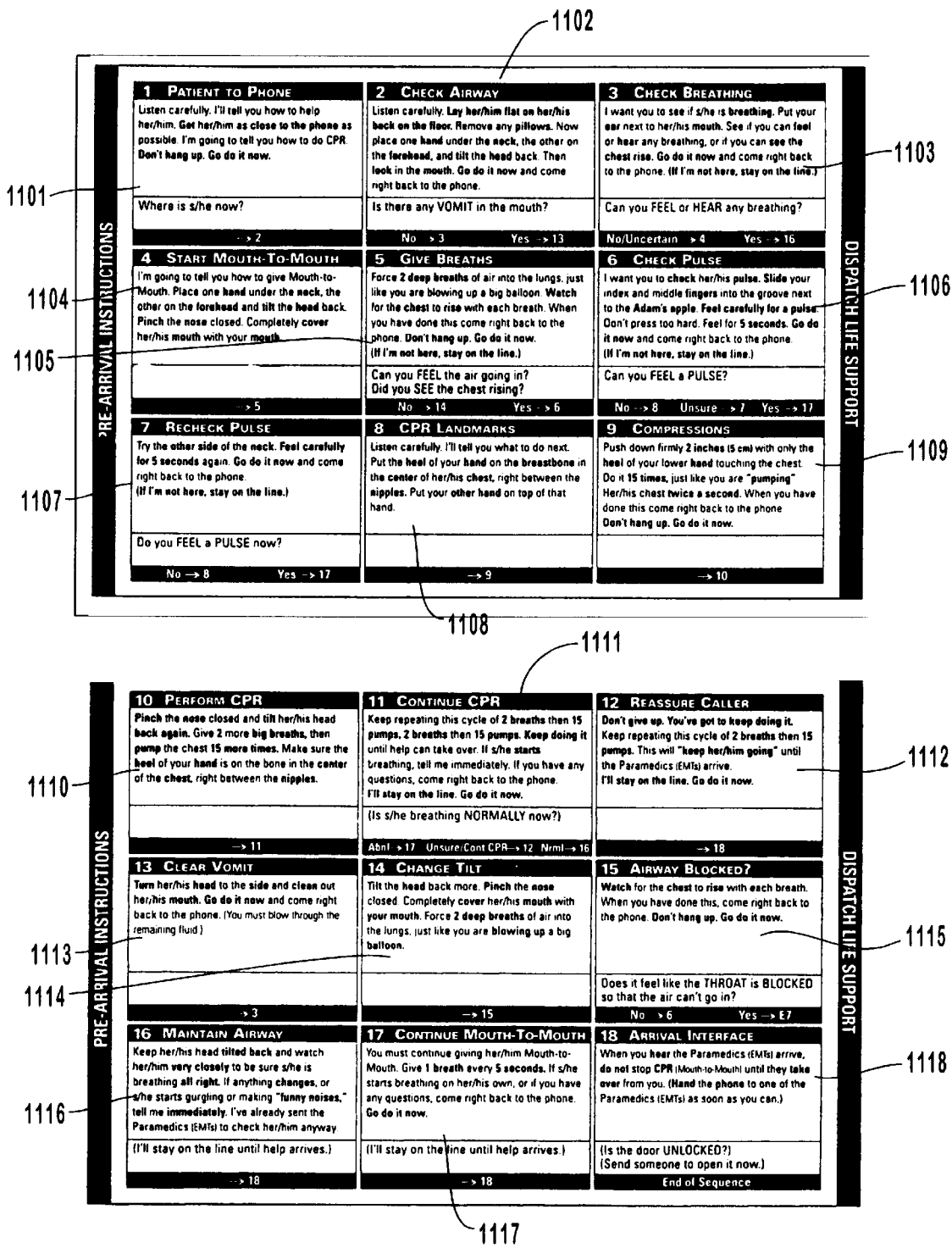
FIG. 11 depicts the preferred embodiment of the flip cards used as one embodiment of this invention, which shows the steps of the arrest-adult pre-arrival instructions protocol of the flip card deck embodiment of the invention.

FIG. 11 depicts the preferred embodiment of the flip cards showing the steps of the arrest—adult pre-arrival instruction protocol invention. The patient to phone step is shown 1101. The check airway step is shown 1102. The check breathing step is shown 1103. The start mouth-to-mouth step is shown 1104. The give breaths step is shown 1105. The check pulse step is shown 1106. The recheck pulse step is shown 1107. The CPR landmarks step os shown 1108. The compressions step is shown 1109. The perform CPR step is shown 1110. The continue CPR step is shown 1111. The reassure caller step is shown 1112. The clear vomit step is shown 1113. The change tilt step is shown 1114. The airway blocked step is shown 1115. The maintain airway step is shown 1116. The continue mouth-to-mouth step is shown 1117. The arrival interface step is shown 1118.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for giving remote emergency medical direction to a dispatcher for patients suffering from distress, comprising the steps of:

(A) providing instructions to an emergency medical dispatcher, including one or more instructions to inquire for specific information, including inquiring if the patient has a pulse and inquiring if the patient can breath normally, receiving response information, and to use said response information to calculate a degree of criticality, informing said emergency medical dispatcher of an appropriate response for dispatch to the patient based on said calculated degree of criticality and dispatching to the patient;

(B) inquiring if the patient has a pulse;

(C) instructing that if unsure, to test again if the patient has a pulse;

(D) instructing on performing CPR;

(E) inquiring if the patient is breathing normally now;

(F) instructing that if unsure if the patient is breathing normally now, reassuring and continuing CPR; and (G) giving remote emergency counsel based upon said inquiries.

2. A system for managing the process of responding to a patient suffering from distress, the system comprising:

(A) a set of instructions, stored on a permanent medium, for use by an emergency medical dispatcher, including instructions to inquire for specific information, including inquiring if the patient has a pulse and inquiring if the patient can breath normally, to receive response information, and to use said response information to calculate a degree of criticality, a means for informing said emergency medical dispatcher of an appropriate emergency medical response for dispatch to the patient based upon said calculated degree of criticality;

said stored instructions further comprising:

(B) a first inquiry as to whether the patient has a pulse;

(C) if pulse is uncertain, a second inquiry as to whether the patient has a pulse;

(D) an instruction on performing CPR;

(E) a third inquiry as to whether the patient is breathing normally now; and (F) if unsure if the patient is breathing normally now, an instruction to reassure and continue CPR.

3. A method for managing the process for responding to an emergency medical call relating to a patient in distress by using a general purpose computer system comprising:

a central processing unit;

dynamic memory, static memory, a display device, an input device, an output device, a mass storage device which contains
   a number of emergency medical instruction records,
   a number of medical information records,
   a grouping of determinant codes,
   a number of emergency medical inquiry reports, the method comprising the steps of:

(A1) displaying on said display device instructions to an emergency medical dispatcher, including instructions to inquire for specific information, said specific information including whether the patient has a pulse and whether the patient can breath normally, (A2) receiving into said general purpose computer, using said input device, responses to said inquiries, (A3) processing in said general purpose computer said input responses, (A4) computing a degree of criticality, and (A5) informing said emergency medical dispatcher of an appropriate response for dispatch to the patient based on said calculated degree of criticality and dispatching to the patient;

(B) receiving on said input device data indicating whether the patient has a pulse;

(C) displaying on said display device an instruction that if uncertain whether the patient has a pulse, to test again if the patient has a pulse;

(D) displaying on said display device an instruction on performing CPR;

(E) displaying on said display device in instruction on testing if the patient is breathing normally after said step of performing CPR;

(F) displaying on said display device an instruction that if unsure whether the patient is breathing normally after said testing step, to reassure and to continue CPR; and (G) computing a determinant value for identifying an appropriate emergency medical response for dispatch to the patient based on whether the patient is breathing and has a pulse and dispatching said appropriate emergency medical response to the patient.

* * * * *